(12) United States Patent
Siminak et al.

(10) Patent No.: US 8,323,236 B1
(45) Date of Patent: Dec. 4, 2012

(54) ANIMAL BREAST PUMP DEVICE

(76) Inventors: Katherine L. Siminak, Arvada, CO (US); Jinae K. Siminak, Arvada, CO (US)

(*) Notice: Subject to any disclaimer, the term of this patent is extended or adjusted under 35 U.S.C. 154(b) by 0 days.

(21) Appl. No.: 13/087,978

(22) Filed: Apr. 15, 2011

(51) Int. Cl.
*A61M 1/06* (2006.01)
(52) U.S. Cl. .......................................... 604/74; 604/73
(58) Field of Classification Search ............... 604/73–76
See application file for complete search history.

(56) References Cited

U.S. PATENT DOCUMENTS

| | | | |
|---|---|---|---|
| 4,573,969 A | | 3/1986 | Schlensog et al. |
| 4,680,028 A | * | 7/1987 | Stuart .............................. 604/74 |
| 4,761,160 A | * | 8/1988 | Vermillion ....................... 604/76 |
| 4,892,517 A | | 1/1990 | Yuan et al. |
| 6,070,915 A | * | 6/2000 | Luo ............................ 285/125.1 |
| 6,383,163 B1 | * | 5/2002 | Kelly et al. ...................... 604/74 |
| 6,609,515 B2 | * | 8/2003 | Bienvenu et al. ......... 128/200.21 |
| 7,267,662 B1 | | 9/2007 | Kirchner |
| 7,824,361 B2 | * | 11/2010 | Luzbetak et al. ................ 604/74 |
| 2007/0022961 A1 | * | 2/2007 | Wheeler ...................... 119/14.01 |
| 2007/0083154 A1 | * | 4/2007 | Sauvageau ....................... 604/73 |
| 2008/0065001 A1 | * | 3/2008 | DiNucci et al. .................. 604/19 |
| 2008/0167605 A1 | * | 7/2008 | Torvik ............................... 604/74 |
| 2010/0010435 A1 | * | 1/2010 | McCrary et al. ................. 604/73 |
| 2010/0174232 A1 | | 7/2010 | Wortley et al. |

* cited by examiner

*Primary Examiner* — Quynh-Nhu H Vu

(57) ABSTRACT

The animal breast pump device provides an extraction mechanism having a cylindrical horizontal T section having a first end spaced apart from a second end with a bottom male thread disposed downwardly on the T section, a cylindrical plunger pump disposed on T section first end, a cylindrical union removably disposed on the T section male thread, a suction funnel removably and threadably disposed on the union, a flexible retainer disposed centrally within the suction funnel, and a bottle having an upwardly disposed female thread, the female thread removably fitted to the T section bottom male thread.

6 Claims, 4 Drawing Sheets

ANIMAL BREAST PUMP DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

Be it known that we, Katherine L. Siminak and Jinae K. Siminak, both citizens of the United States, have invented new and useful improvements in an animal breast pump device as described in this specification.

BACKGROUND OF THE INVENTION

Breast pumps are well known for use with humans, with fewer devices being suited to animal use. Dogs provide an excellent example wherein a breast pump can be a particularly useful device. Zoo animals provide further example. The present device is ideal for use on a variety of animals.

FIELD OF THE INVENTION

The animal breast pump device relates to breast pumps and more especially to a breast pump particularly suited to animal use.

SUMMARY OF THE INVENTION

The general purpose of the animal breast pump device, described subsequently in greater detail, is to provide an animal breast pump device which has many novel features that result in an improved animal breast pump device which is not anticipated, rendered obvious, suggested, or even implied by prior art, either alone or in combination thereof.

To attain this, the animal breast pump device provides a tool for extracting and storing an animal's breast milk. Importantly, the device's makeup is ideal for a human to use, especially with horizontally disposed T section and accompanying fittings. The plunger pump, whether manual or electric, is fitted horizontally to the T section first end. The union is fitted to the T section second end. The union may be a right angle or may be comprised of a flex hose. The suction funnel is removably fitted to the union. The suction funnel importantly further importantly comprises a centrally disposed flexible retainer for selective retention on the animals teat. The horizontally disposed pump allows a user to easily and effectively position the suction funnel on the animal's teat and then operate the pump from a preferably significantly lateral position. The flex hose union allows further operational liberty, with both union embodiments importantly providing ideal positioning for a user and an animal. The manual pump embodiment importantly provides a cylindrical T-handle with spaced apart finger grooves for best grip, along with the finger grip disposed downwardly on the plunger pump itself.

The plurality of bottles provided is importantly upwardly female threaded for ease of joining to and removal from the T section. Larger animals, for example, may require several bottles for complete milk extraction.

Importantly, the device components are designed to easily assemble and disassemble for sanitation and for storage. The relationship and shape of the components are important to function.

Thus has been broadly outlined the more important features of the improved animal breast pump device so that the detailed description thereof that follows may be better understood and in order that the present contribution to the art may be better appreciated.

An object of the animal breast pump device is to extract milk from an animal.

Another object of the animal breast pump device is to provide for selective retention to an animal.

A further object of the animal breast pump device is to provide ideals angles of fit and operation for the user.

An added object of the animal breast pump device is to enable easy sanitation.

And, an object of the animal breast pump device is to provide for manual milk pumping.

Another object of the animal breast pump device is to provide for electrical milk pumping.

These together with additional objects, features and advantages of the improved animal breast pump device will be readily apparent to those of ordinary skill in the art upon reading the following detailed description of presently preferred, but nonetheless illustrative, embodiments of the improved animal breast pump device when taken in conjunction with the accompanying drawings.

DETAILED DESCRIPTION OF THE DRAWINGS

With reference now to the drawings, and in particular FIGS. 1 through 6 thereof, the principles and concepts of the animal breast pump device generally designated by the reference number 10 will be described.

Figure 4:
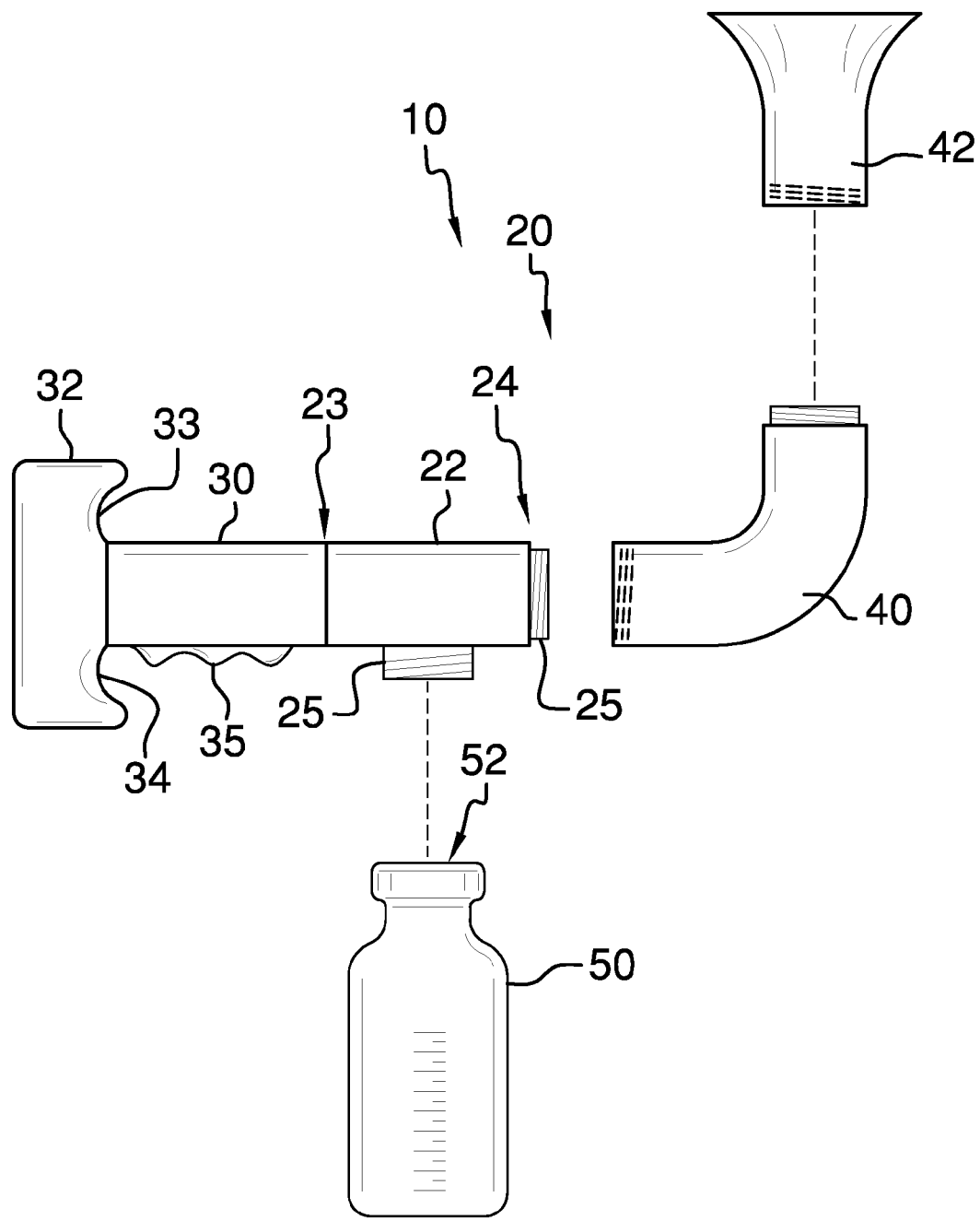
FIG. 4 is an exploded lateral elevation view.

Referring to FIG. 4, the device 10 partially comprises the extraction mechanism 20. The extraction mechanism 20 comprises a cylindrical horizontal T section 22 having a first end 23 spaced apart from a second end 24. The male thread 25 is disposed on the second end 24. The bottom male thread 26 is disposed downwardly on the T section 22. The cylindrical plunger pump 30 is disposed on T section 22 first end 23.

Figure 1:
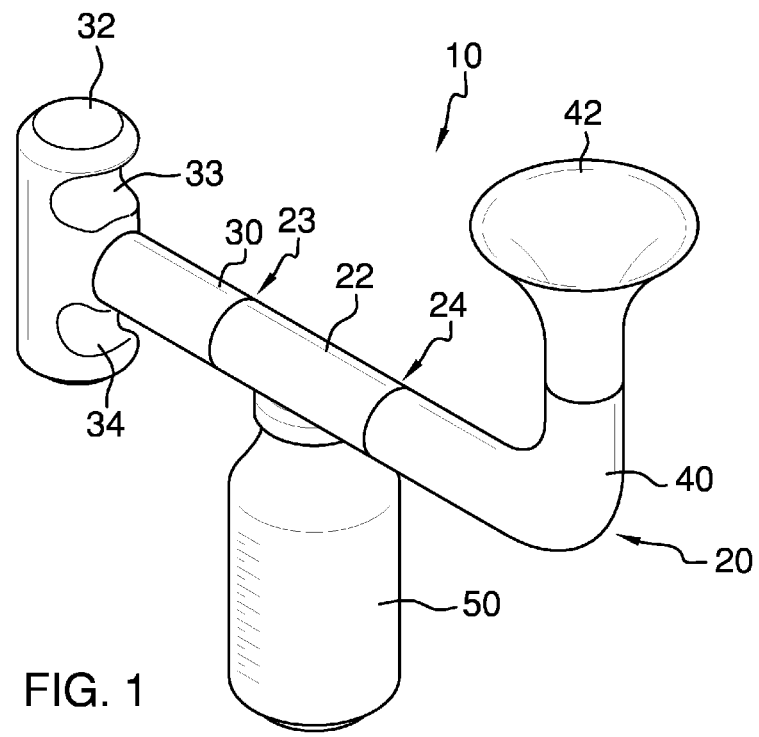
FIG. 1 is a perspective view.

Referring to FIG. 1, the cylindrical T-handle 32 is disposed outwardly and perpendicularly on the cylindrical plunger pump 30. An upper finger groove 33 is disposed medially on the cylindrical T-handle 32. The upper finger groove 33 is disposed above the cylindrical plunger pump 30. The lower finger groove 34 is disposed medially on the cylindrical T-handle 32. The lower finger groove 34 is disposed below the cylindrical plunger pump 30.

Referring again to FIG. 4, the finger grip 35 is disposed downwardly on the cylindrical plunger pump 30.

Figure 2:
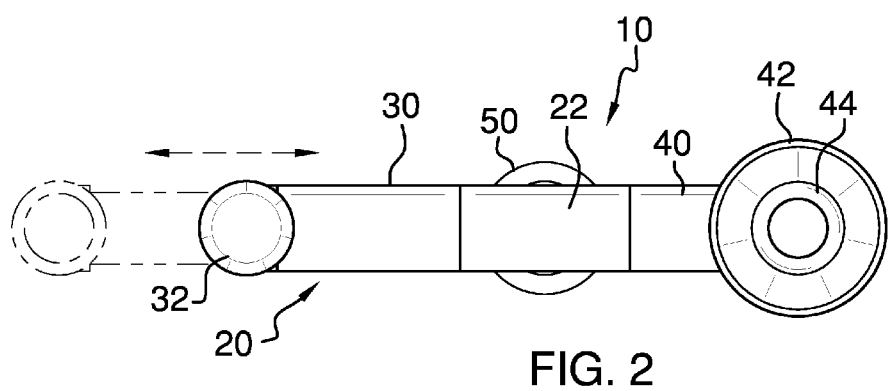
FIG. 2 is a top plan view.
Figure 3:
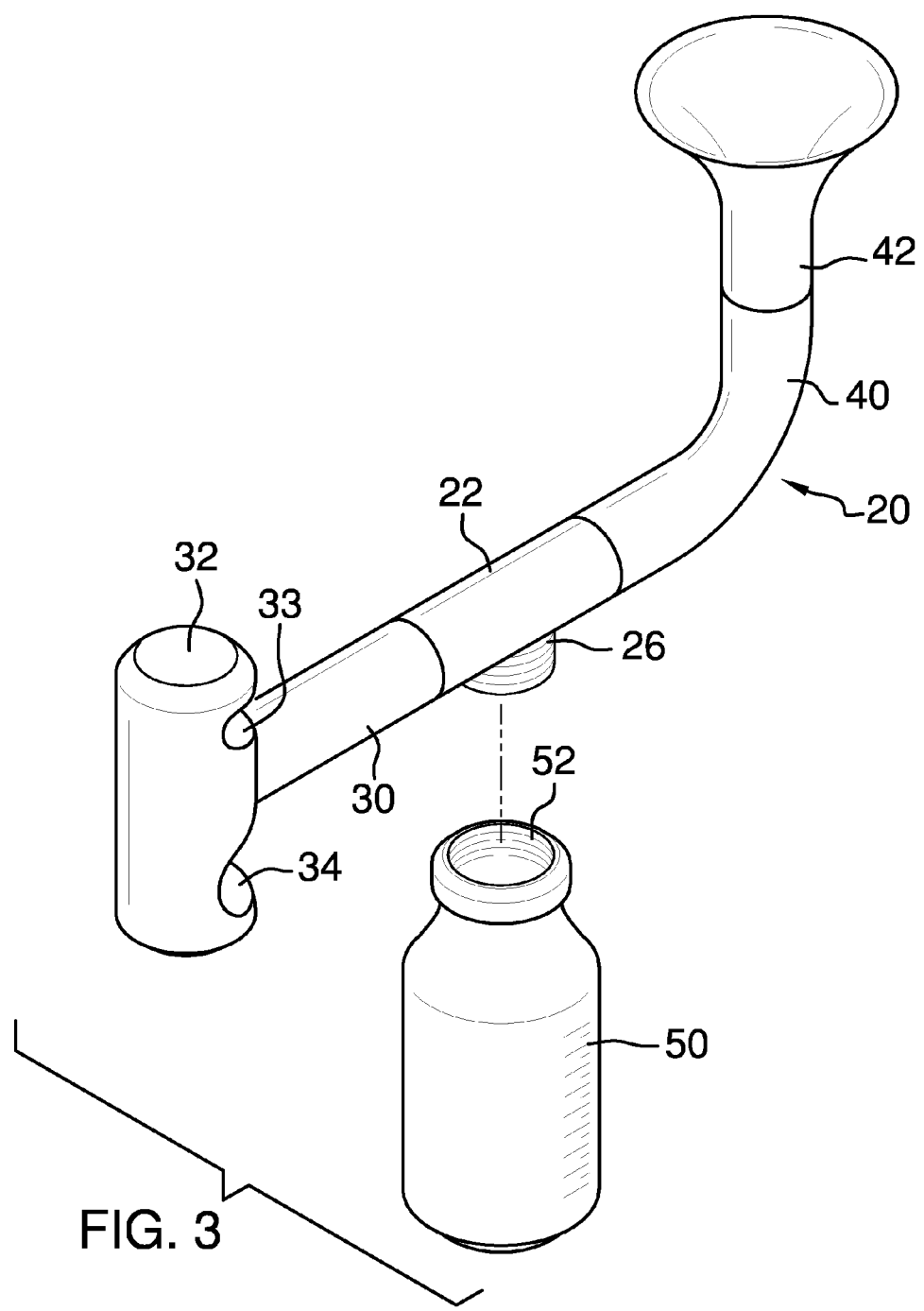
FIG. 3 is a perspective view, bottle removed from the extraction mechanism.
Figure 5:
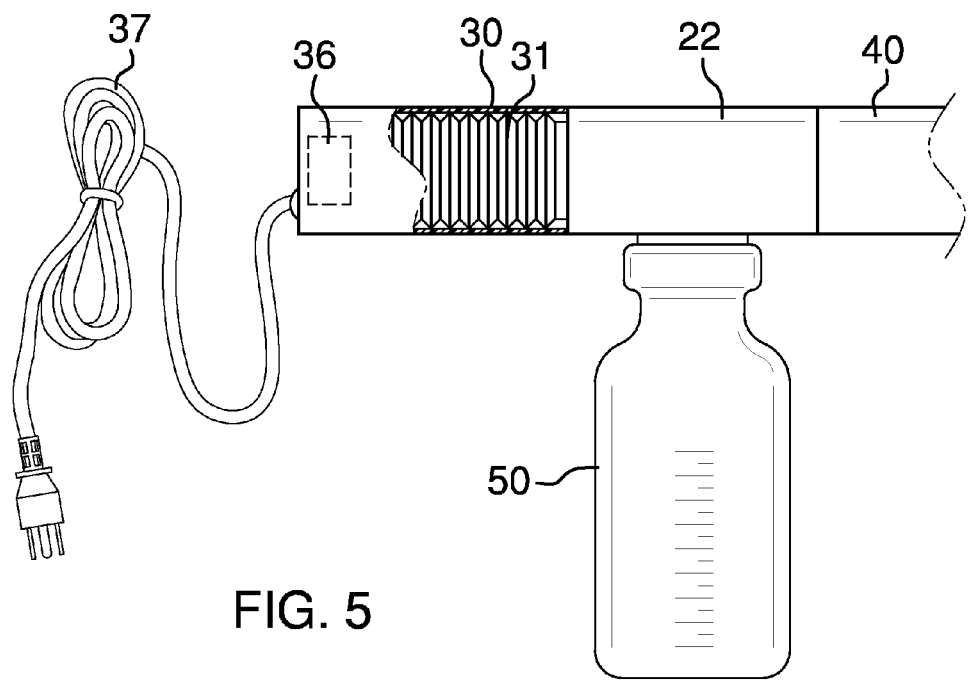
FIG. 5 is a lateral elevation view, with electrically operated extraction mechanism.

Referring to FIG. 2, a user may hold the finger grip 35 with one hand while grasping the cylindrical T-handle 32 with finger grooves with the other, thereby moving the cylindrical T-handle 32 inwardly and outwardly to operate the extraction mechanism 20. The functional comfort of the design of each of these extraction mechanism 20 components is extremely important in ease of repetitive use. Referring to FIG. 5, the accordion 31 is disposed within the plunger pump 30. In this embodiment, the electrical motor 36 is disposed laterally within the plunger pump 30. A power cord 37 is affixed to the motor 36.

Referring to FIG. 2, the manually operated plunger pump 30 is provided, in an alternate embodiment to the motorized pump 30. Both operate with the accordion 31.

Referring to FIG. 3 and again to FIG. 4, the right angle cylindrical union 40 is removably disposed on the T section 22 male thread 25. The suction funnel 42 is removably and threadably disposed on the cylindrical union 40.

Referring to FIG. 2, the flexible retainer 44 is disposed centrally within the suction funnel 42 and importantly aids in selective nipple retention.

Referring to FIG. 4, the bottle 50 has an upwardly disposed female thread 52. The female thread 52 is removably fitted to the T section 22 bottom male thread 26.

Figure 6:
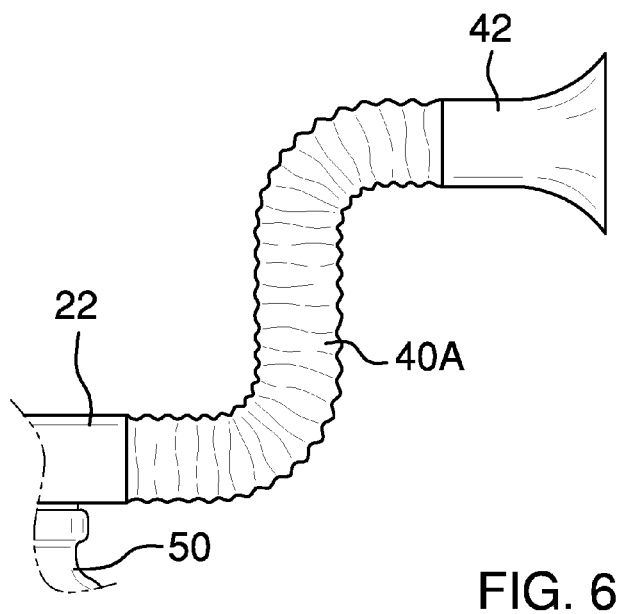
FIG. 6 is a lateral elevation view of the flexible union.

Referring to FIG. 6, the optional flex hose union 40A is provided and importantly aids in adapting to various animals and their given positions.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the animal breast pump device may be used.

What is claimed is:

1. An animal breast pump device comprising, in combination:
   an extraction mechanism comprising:
      a cylindrical horizontal T section having a first end spaced apart from a second end;
      a male thread disposed on the second end;
      a bottom male thread disposed downwardly on the T section;
      a cylindrical plunger pump disposed on T section first end;
      an accordion disposed within the cylindrical plunger pump;
      a cylindrical T-handle disposed outwardly and perpendicularly on the cylindrical plunger pump;
      an upper finger groove disposed medially on the cylindrical T-handle, the upper finger groove disposed above the cylindrical plunger pump;
      a lower finger groove disposed medially on the cylindrical T-handle, the lower finger groove disposed below the cylindrical plunger pump;
      a finger grip disposed downwardly on the cylindrical plunger pump;
      a cylindrical union removably disposed on the T section male thread;
      a suction funnel removably and threadably disposed on the cylindrical union;
      a flexible retainer disposed centrally within the suction funnel;
      a bottle having an upwardly disposed female thread, the female thread removably fitted to the T section bottom male thread.

2. The device according to claim 1 wherein the cylindrical union further comprises a right angle union.

3. The device according to claim 1 wherein the cylindrical union further comprises a flex hose union.

4. An animal breast pump device comprising, in combination:
   an extraction mechanism comprising:
      a cylindrical horizontal T section having a first end spaced apart from a second end;
      a male thread disposed on the second end;
      a bottom male thread disposed downwardly on the T section;
      a cylindrical plunger pump disposed on T section first end;
      an accordion disposed within the plunger pump;
      a motor disposed laterally within the plunger pump;
      a power cord affixed to the motor;
      a cylindrical union removably disposed on the T section male thread;
      a suction funnel removably and threadably disposed on the cylindrical union;
      a flexible retainer disposed centrally within the suction funnel;
      a bottle having an upwardly disposed female thread, the female thread removably fitted to the T section bottom male thread.

5. The device according to claim 4 wherein the cylindrical union further comprises a right angle union.

6. The device according to claim 4 wherein the cylindrical union further comprises a flex hose union.

* * * * *